United States Patent [19]
Murphy et al.

[11] Patent Number: 5,628,990
[45] Date of Patent: May 13, 1997

[54] ANHYDROUS COSMETIC PRODUCT CONTAINING DEODORANT AND DESICCANT INGREDIENTS

[75] Inventors: Richard T. Murphy, Belle Mead; Wolfgang R. Bergmann, Princeton, both of N.J.

[73] Assignee: Church & Dwight Co., Inc., Princeton, N.J.

[21] Appl. No.: 548,150

[22] Filed: Oct. 25, 1995

[51] Int. Cl.$^6$ .................... A61K 7/32; C01B 35/00
[52] U.S. Cl. .................... 424/65; 423/265; 423/267; 423/275; 423/422; 424/400; 424/401; 424/DIG. 5
[58] Field of Search .................... 424/65, 400, 401, 424/DIG. 5; 423/265, 267, 275, 422

[56] References Cited

U.S. PATENT DOCUMENTS

| | | | |
|---|---|---|---|
| 4,049,792 | 9/1977 | Elsnau | 424/66 |
| 4,382,079 | 5/1983 | Marschner | 424/65 |
| 4,511,554 | 4/1985 | Geria et al. | 424/65 |
| 4,822,602 | 4/1989 | Sabetelli | 424/65 |
| 4,832,945 | 5/1989 | Osipow et al. | 424/65 |
| 4,980,156 | 12/1990 | Raleigh et al. | 424/66 |
| 4,985,238 | 1/1991 | Tanner | 424/66 |
| 5,422,087 | 6/1995 | Lajoie | 423/267 |

*Primary Examiner*—Shelley A. Dodson
*Attorney, Agent, or Firm*—Irving M. Fishman

[57] ABSTRACT

This invention provides cosmetic deodorant stick, roll-on and cream formulations. An invention deodorant product comprises an organic matrix having a dispersed solids phase which includes discrete crystallites of bicarbonate salt ingredient and particulate boron oxide desiccant ingredient. When an invention deodorant product is applied to a skin surface, the boron oxide reacts with moisture, and converts to boric acid which neutralizes any content of a strong basic irritant such as alkali metal carbonate which is present as an impurity in an alkali metal bicarbonate salt.

28 Claims, No Drawings

ANHYDROUS COSMETIC PRODUCT CONTAINING DEODORANT AND DESICCANT INGREDIENTS

BACKGROUND OF THE INVENTION

Antiperspirants combat axillary odors by inhibiting perspiration through the action of astringent salts such as aluminum and zinc salts, but may be irritating to a large number of users. Deodorants function by neutralizing the objectionable odors resulting from the degradation of several components of perspiration by chemical and microbial action into malodorous fatty acids.

Numerous solid antiperspirant and/or deodorant compositions have been described in the chemical and cosmetic literature. These compositions generally are emulsion sticks or suspensoid sticks. Emulsion sticks contain a solution of the antiperspirant ingredient incorporated into the stick via an emulsion. Although emulsion sticks are desirable in certain respects, they tend to be unstable, exhibit tackiness, and leave a visible residue on the skin after use. Suspensoid sticks contain the powdered antiperspirant ingredient suspended in the stick without the use of water or an emulsion. While suspensoids have stability, they tend to leave a white chalky residue on the skin after application.

Manufacturers have found that anhydrous antiperspirant stick systems are more marketable and have good consumer acceptance primarily due to the ease of application to the skin, good cosmetic esthetics and an acceptable degree of effectiveness. Previous to the development of anhydrous stick systems, numerous water based systems were developed in which the active astringent salts were solubilized in a thickened or gelled composition. This is exemplified in U.S. Pat. Nos. 2,732,327; 2,857,315; 3,255,082; and 3,928,557. The water based systems are difficult to apply to the skin, and their consistency and effectiveness are variable.

Many anhydrous stick compositions have been described in the literature which attempt to improve the delivery and the effectiveness of their antiperspirant and deodorant characteristics. Antiperspirant stick systems consisting of low molecular weight monohydric alcohols in conjunction with polyhydric alcohols are described in U.S. Pat. No. 4,137,306. These sticks have the advantage of quicker drying rates, but the residue of the polyhydric alcohols in combination with the astringent salts produces a high degree of tack, and their effectiveness is limited to the type and amount of astringent salts that could be incorporated in the stick matrix.

Anhydrous stick compositions that suspend the aluminum salt in a hydrophobic matrix are described in U.S. Pat. No. 4,049,792. These compositions employ waxy materials and long chain fatty esters to form a stick that delivers the active astringent salts to the skin.

Cosmetic stick compositions made in accordance with these embodiments are greasy, and the active astringent salt is enveloped in a manner that prevents maximum performance. To alleviate this inherent negative characteristic, volatile silicone fluids replacement of the less volatile long chain fatty esters is described in U.S. Pat. No. 4,126,679. This disclosure teaches the advantage of utilizing a volatile non-staining liquid such as cyclic dimethylpolysiloxanes (referred to as volatile silicones), in combination with various types of waxes, as a carrier for the active astringent salts in an antiperspirant stick composition. Similar antiperspirant stick compositions containing volatile silicones are described in U.S. Pat. Nos. 4,511,554; 4,980,156; and 4,985,238.

With respect to deodorant activity, sodium bicarbonate has long been recognized for its deodorant properties, and has commonly been used as a household deodorant. Plain powdered sodium bicarbonate, or sodium bicarbonate diluted with talc or other filler, has been used as an underarm deodorant as disclosed in U.S. Pat. No. 4,382,079. Other publications which describe cosmetic stick compositions containing a bicarbonate deodorant include U.S. Pat. No. 4,822,602 and U.S. Pat. No. 4,832,945.

However, the development of a practical and effective antiperspirant composition in cosmetic stick form which is also capable of deodorization, and which is capable of consumer acceptability, presents many factors which are unique. Because sodium and potassium bicarbonate have only limited solubility in water, alcohol and other solvents, the preparation of a composition suitable for dispensing in cosmetic stick form has involved many processing obstacles. In addition to the problem of limited solubility, sodium bicarbonate often is incompatible with the active astringent salts and with other ingredients of conventional stick compositions. Also, the dimensional stability of the cosmetic stick containing sodium bicarbonate, and the esthetic appearance and the "feel" on the skin, are just a few of the additional difficulties encountered in the preparation of a low residue cosmetic deodorant or antiperspirant-deodorant product.

Another significant problem associated with the incorporation of a bicarbonate deodorant ingredient in a cosmetic stick roll-on or cream formulation is the tendency for the high density bicarbonate salt particles to settle in the fluid medium during processing. Also, under the elevated temperature conditions required for the admixing and blending of ingredients, bicarbonate degradation and evolution of carbon dioxide occur.

There is continuing interest in the development of improved cosmetic products which exhibit deodorant activity, or antiperspirant-deodorant activity.

Accordingly, it is an object of this invention to provide a cosmetic stick roll-on or cream product which exhibits deodorant properties, and is characterized by excellent esthetics and cosmetic properties.

It is another object of this invention to provide a homogeneous cosmetic deodorant product which contains a dispersed phase of particulate deodorant and desiccant ingredients in an organic matrix phase.

It is another object of this invention to provide a homogeneous deodorant product which contains a dispersed particle phase of polymer-encapsulated bicarbonate salt crystallites, and which is dimensionally stable.

Other objects and advantages of the present invention shall become apparent from the accompanying description and examples.

DESCRIPTION OF THE INVENTION

One or more objects of the present invention are accomplished by the provision of a cosmetic deodorant product comprising an organic matrix which contains a homogeneously dispersed particulate phase which comprises (1) between about 0.5–20 weight percent of discrete crystallites of at least one ingredient selected from alkali metal and ammonium bicarbonates, and (2) between about 0.01–5 weight percent of particulate boron oxide desiccant ingredient, based on product weight.

A present invention cosmetic deodorant product normally is in the form of a cosmetic stick, roll-on or cream formulation.

The bicarbonate salt crystallites can have an average particle size between about 1–200 microns. The boron oxide crystallites can have an average particle size between 0.1–200 microns. A preferred range for both bicarbonate and boron oxide crystallites is an average particle size between about 1–80 microns.

The term "discrete" as employed herein refers to crystallites which are individually distinct solids.

The term "average particle size" as employed herein refers to the average of the largest dimension of the particles.

The particulate bicarbonate salt starting material of an invention powder composition is selected from alkali metal and ammonium bicarbonates, such as sodium bicarbonate, potassium bicarbonate and ammonium bicarbonate, and mixtures thereof.

The boron oxide ingredient also is referred to as boron anhydride ($B_2O_3$) in the chemical literature. Boron oxide exists in both crystalline and glass forms. Boron oxide solids can be ground into an ultrafine powder.

Impurities present in boron oxide include metaboric acid ($HBO_2$) and boric acid ($H_3BO_3$). Reagent grade boron oxide can have a purity of 99.999%.

The boron oxide ingredient functions as a potent desiccant when an invention cosmetic deodorant product has been formulated. It readily absorbs trace amounts of moisture and maintains a cosmetic deodorant product in an anhydrous state. When an invention cosmetic product is applied to human skin such as underarm areas, the boron oxide absorbs moisture exuded by the skin. The boron oxide keeps the skin comfortably dry, as the boron oxide is converting to boric acid via metaboric acid.

The transient boric acid byproduct has a soothing effect on the applied skin area. The boric acid functions as a neutralizing agent with respect to any strong basic irritant such as alkali metal carbonate when it is an impurity in the alkali metal bicarbonate ingredient.

Boric acid is a weak and exclusively monobasic acid that is not a proton donor, but acts as a Lewis acid by accepting hydroxyl anions ($OH^-$):

$$B(OH)_3 + H_2O \rightleftharpoons B(OH)_4^- + H^+$$

$$K = 6 \times 10^{-10}$$

Boric acid can react with a strong base such as sodium carbonate. Boric acid does not react with a weak base such as sodium bicarbonate, but is susceptible to complex formation with the bicarbonate salt under the conditions prevalent when a present invention cosmetic product is applied to underarm skin areas to obtain a deodorizing effect during daily personal hygiene usage.

A present invention cosmetic deodorant product can be formulated originally with a homogeneously dispersed particulate phase which can contain between about 0.01–3 weight percent of discrete crystallites of boric acid ingredient, based on product weight. The boric acid can be in addition to the boron oxide ingredient, or can be a substitute therefor.

Commercial grade alkali metal bicarbonate bulk commodities typically have a content of alkali metal carbonate, which is a residual byproduct of the manufacturing process. Substantially all of the commercial grade alkali metal bicarbonate is produced by carbonation of an aqueous solution of alkali metal carbonate:

$$Na_2CO_3 + H_2O + CO_2 \rightarrow NaHCO_3$$

A residual quantity (e.g., 0.05–2 weight percent) of alkali metal carbonate is adsorbed as a contaminant on the surfaces of the crystalline alkali metal bicarbonate particles.

The presence of alkali metal carbonate in bulk alkali metal bicarbonate powder is attributable also to an additional factor. Alkali metal bicarbonate decomposes to alkali metal carbonate at elevated temperatures above about 100° C. At ambient temperatures, alkali metal bicarbonate converts to alkali metal carbonate at a constant slow rate. Typically, the initial residual alkali metal carbonate content is less than about one weight percent of the bulk alkali metal bicarbonate powder.

A reaction occurs between alkali metal carbonate impurity and boric acid during the time period that a present invention cosmetic deodorant product is on a skin surface after application.

$$B_2O_3 + H_2O \rightarrow HBO_2 + H_3BO_3$$

$$Na_2CO_3 + HBO_2 + H_3BO_3 \rightarrow NaHCO_3 + NaBO_2 + NaH_2BO_3$$

The byproduct borates are anhydrous when initially formed, and provide an extended drying effect by absorbing skin surface moisture.

In another embodiment the alkali metal bicarbonate ingredient can comprise crystallites which are in the form of organic-encapsulated particles. During a coating procedure, crystallites with a transient liquid surface coating can make contact and coalesce into larger encapsulated particles with a content of multiple crystallites.

The application of the organic coating to the alkali metal bicarbonate ingredient crystallite surfaces is accomplished by conventional means such as pan coating, fluidized coating, centrifugal fluidized coating, and the like. The organic coating phase usually is dissolved in a suitable solvent such as water, methanol, ethanol, acetone, tetrahydrofuran, ethyl acetate, dimethylformamide, and the like, as appropriate for a selected organic species. A coating phase also can be applied in the form of an emulsion or suspension. After the coating medium is applied to the crystallites, the solvent medium is removed by evaporation, thereby forming a continuous film coating which encapsulates the discrete fine grain crystallites.

In a preferred coating procedure, bicarbonate powder is dispersed in an aqueous medium which contains a coating polymer ingredient. The aqueous dispersion is atomized and sprayed into heated air to remove the aqueous phase, and to provide a free-flowing polymer-encapsulated bicarbonate powder product.

The coating thickness on the alkali metal bicarbonate crystallite surfaces typically will vary in the range between about 0.1–20 microns. The coating can consist of a single layer or multiple layers. The organic coating can constitute between about 5–70 weight percent of the total dry weight of the coated crystallites.

A polymer employed for coating the bicarbonate crystallites is selected from hydrophilic organic polymers and hydrophobic (water-insoluble) organic polymers and mixtures thereof.

A hydrophilic polymer employed for coating the bicarbonate crystallites is selected from water-soluble and water-dispersible organic polymers. A mixture of polymers can be employed, and a content of between about 0.5–40 weight percent of a water-insoluble polymer, based on the coating weight, can be included with a hydrophilic polymer.

The term "hydrophilic" as employed herein refers to an organic species which has a water-solubility of at least about one gram per 100 grams of water at 25° C. The term "hydrophobic" or "water-insoluble" as employed herein refers to an organic species which has a water solubility of less than about one gram per 100 grams of water at 25° C.

Suitable hydrophilic compounds and polymers for coating ingredient crystallites include gum arabic, gum karaya, gum tragacanth, guar gum, locust bean gum, xanthan gum, carrageenan, alginate salt, casein, dextran, pectin, agar, sorbitol, 2-hydroxyethyl starch, 2-aminoethyl starch, maltodextrin, amylodextrin, 2-hydroxyethyl cellulose, methyl cellulose, carboxymethyl cellulose salt, cellulose sulfate salt, polyvinylpyrrolidone, polyethylene glycol, polypropylene glycol, polyethylene oxide, polyvinyl alcohol/acetate, polyacrylamide, and the like. Polyvinyl acetate is illustrative of a water-insoluble polymer which can be included as an additional coating component to moderate the hydrophilicity of a hydrophilic polymer coating.

Suitable water-insoluble polymers, alone or in combination with one or more other components, for coating ingredient crystallites include polyvinyl acetate, polyacrylamide, polyvinyl chloride, polystyrene, polyethylene, polyurethane, and the like.

The rate of release of core matrix bicarbonate salt content of the particles under moisture conditions can be controlled by the quantity and type of organic coating on the particle surfaces.

Low molecular weight hydrophilic polymers will release the particle core matrix content at a relatively fast rate in the presence of moisture. High molecular weight polymers which are less hydrophilic will release at a relatively slow rate. Additional rate control can be obtained by employing mixtures of polymer components of varied hydrophilicity.

Polyethylene glycol (M.W. of 4000) or polyvinyl alcohol will release the particle core matrix content at a relatively fast rate. Polyethylene oxide (M.W. of 4,000,000) or partially hydrolyzed polyvinyl acetate will release at a relatively slow rate. Polyvinylpyrrolidone will release the particle core matrix content at an intermediate rate when in contact with underarm type of moisture.

In another embodiment this invention provides a cosmetic stick product consisting of a solid organic matrix comprising the following parts by weight of ingredients:

| | |
|---|---|
| volatile oil | 10–55 |
| liquid emollient | 1–35 |
| low melting point wax | 12–30 | and the solid organic matrix contains a homogeneously dispersed particulate phase which comprises (1) between about 0.5–20 weight percent of discrete crystallites of at least one ingredient selected from alkali metal and ammonium bicarbonates, and (2) between about 0.01–5 weight percent of particulate boron oxide desiccant ingredient, based on product weight.

In another embodiment this invention provides a cosmetic roll-on product consisting of a liquid matrix comprising the following parts by weight of ingredients:

| | |
|---|---|
| volatile oil | 55–70 |
| liquid emollient | 3–10 | and the liquid organic matrix contains a homogeneously dispersed particulate phase which comprises (1) between about 0.5–20 weight percent of discrete crystallites of at least one ingredient selected from alkali metal and ammonium bicarbonates, and (2) between about 0.01–5 weight percent of particulate boron oxide desiccant ingredient, based on product weight.

A present invention cosmetic stick, roll-on or cream deodorant product can contain between about 0.1–20 weight percent of an antiperspirant compound as an additional ingredient.

An invention antiperspirant-deodorant cosmetic stick product typically contains the following weight proportions of main ingredients:

| Ingredient | Weight |
|---|---|
| volatile oil | 25–50 |
| liquid emollient | 2–20 |
| wax (MP 95°–180° F.) | 15–20 |
| antiperspirant | 20–28 |
| encapsulated bicarbonate/fragrance powder | 0.1–25 |
| surfactant | 1–3 |

The volatile oil ingredient preferably is selected from silicone and branched-chain hydrocarbon compounds.

A volatile silicone oil ingredient in a cosmetic stick or roll-on product of the present invention preferably is a cyclic or linear polydimethylsiloxane containing between about 3–9 silicon atoms. A suitable cyclic volatile polydimethylsiloxane compound is illustrated by the formula:

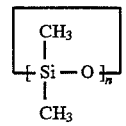

where n is an integer with a value of about 3–7.

A suitable linear polydimethylsiloxane is illustrated by the formula:

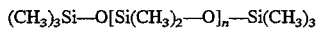

where n is an integer with a value of about 1–7.

Linear volatile silicone compounds generally have viscosities of less than about 5 centistokes at 25° C., while the cyclic type compounds have viscosities of less than about 10 centistokes.

Typical of the volatile silicone compounds that can be employed for purposes of the present invention is cyclomethicone, which is a cyclic dimethylpolysiloxane conforming to the above formula where n averages between 3–6. Dow Corning 245 Fluid (Dow Corning) is a cyclic volatile silicone which is commercially available. CTFA Cosmetic Ingredient Dictionary, Third Edition, (Estrin et al., Editors; The Cosmetic, Toiletry and Fragrance Association, Inc.; 1982) lists cyclic silicones on page 60, under the entry "Cyclomethicone".

A volatile hydrocarbon oil type of ingredient preferably is a $C_{12}$–$C_{20}$ branched-chain hydrocarbon compound or mixture. Suitable volatile branched-chain hydrocarbon oils include isododecane ($C_{12}$), isohexadecane ($C_{16}$), isoeicosane ($C_{20}$), and the like. These types of branched-chain hydrocarbons are marketed by Permethyl Corporation under tradenames such as Permethyl 99A, Permethyl 101A and Permethyl 102A.

The liquid emollient ingredient of an invention cosmetic stick, roll-on or cream deodorant product is selected from one or more water-insoluble organic compounds which are liquid at 25° C. and which contribute a combination of properties that are advantageous in an invention cosmetic stick or roll-on product.

The term "water-insoluble" as employed herein refers to an emollient ingredient which has a water-solubility of less than about one weight percent at 25° C.

A present invention emollient ingredient exhibits a low degree of irritation and toxicity in topical applications, and provides a softening or soothing effect on surface skin tissue.

Preferred water-insoluble liquid emollients include fatty alcohols such as oleyl, lauryl and hexadecyl; esters such as diisopropyl adipate, benzoic acid esters of $C_9$-$C_{15}$ alcohols, and isononyl isononanoate; alkanes such as mineral oil; silicones such as dimethylpolysiloxane and cyclic dimethylpolysiloxane; and ethers such as polyoxypropylene butyl ether and polyoxypropylene cetyl ether. Preferred water-insoluble liquid emollients include diisopropyl adipate, 2-ethylhexyl palmitate, dimethylpolysiloxane (50 cst.), and polyoxypropylene (14) butyl ether.

The low melting point wax ingredient of a present invention cosmetic deodorant product comprises one or more organic compounds which have a melting point in the range between about 95°–180° F.

Suitable types of wax-like compounds include fatty alcohols, fatty acid esters, fatty acid amides, and the like, which have an aliphatic chain length between about 8–30 carbon atoms. Illustrative of wax-like compounds are cetyl alcohol, myristyl alcohol, stearyl alcohol, paraffin, and the like, and mixtures thereof.

The low melting point wax ingredient can include up to about 30 weight percent, based on the weight of wax ingredient, of a wax which has a melting point between about 180°–220° F. Illustrative of these higher melting waxes are beeswax, spermaceti, carnauba, bayberry, candelilla,, montan, ozokerite, ceresin, paraffin, castor wax, Fischer-Tropsch waxes, and the like.

The antiperspirant ingredient of a present invention cosmetic stick, roll-on or cream antiperspirant deodorant product typically is a particulate astringent compound which has an average particle size between about 1–100 microns. Superior cosmetic stick properties are obtained if part or all of the antiperspirant ingredient is in the form of particles which have a diameter less than about one micron. Optionally, the antiperspirant ingredient can be pre-coated with a polymer to prevent interaction with the other ingredients, and to provide a sustained-release antiperspirant activity under application conditions.

Suitable astringent compounds include aluminum chloride, aluminum chlorohydrate, aluminum sulfocarbolate, aluminum sulfate, aluminum-zirconium chlorohydrate, zinc sulfate, zinc sulfocarbolate, and zirconium chlorohydrate. Preferred types of astringent compounds are aluminum chlorohydrates and aluminum-zirconium chlorohydrates, such as aluminum-zirconium tetrachlorohydrex glycine. Aluminum-zirconium tetrachlorohydrex glycine is commercially available as Rezal 36 GP Superultrafine (Reheis), and Reach AZP 908 (Reheis).

Other optional ingredients also may be included in an invention cosmetic formulation, such as bacteriostats, fungistats, fillers, stabilizing agents, surfactants, antioxidants, pigments, coloring agents, perfumes, chelating agents, and the like.

A surfactant ingredient of an invention cosmetic formulation is selected from nonionic, cationic and anionic polymers. Suitable surfactant polymers include cetyltrimethylammonium bromide; sodium lauryl sulfate; sodium dodecylbenzene-sulfonate; ammonium lignosulfonate; condensation products of ethylene oxide with fatty alcohols, amines or alkylphenols; partial esters of fatty acids and hexitol anhydrides; polyalkylene glycol esters; and the like. Illustrative of a preferred type of surfactant polymer is polyethylene glycol (PEG) stearate, which is commercially available as PEG 600 distearate.

A bacteriostat such as 2,4,4'-trichloro-2'-hydroxydiphenyl ether (Triclosan) typically is added in a quantity between about 0.08–3 weight percent, based on the weight of the cosmetic stick, roll-on or cream deodorant product.

In another embodiment this invention provides a method of practicing personal hygiene which comprises applying a present invention cosmetic stick, roll-on or cream deodorant product to skin surfaces in a deodorant-effective amount, wherein the initiation and continuation of deodorizing activity is signaled by a perceived dryness and esthetic soothing effect.

Other advantages are provided by the practice of the present invention. As noted in the Background section of the specification, the relative densities of the organic matrix and suspension phases in a cosmetic stick, roll-on or cream product directly affects the stability and esthetics of the formulations.

Density matching of inorganic and organic phases is a significant factor in cosmetic deodorant products. When a present invention formulation contains an optional organic-coated bicarbonate deodorant ingredient, it has a lower density which more closely matches the density of the organic matrix of a cosmetic stick, roll-on or cream product than does uncoated bicarbonate ingredient.

When there is density matching of organic matrix and dispersed organic-coated bicarbonate particle phases, a cosmetic stick, roll-on or cream product has improved dimensional stability, and better esthetic appearance and "feel" when applied to human skin.

In general, the ingredients of a cosmetic deodorant formulation can be blended in any order. However, in the practice of a process for manufacture of a present invention cosmetic product there is advantage in utilizing a phased order of ingredient addition and blending under controlled temperature conditions. Additional advantage is obtained in the process if there is a minimal time lapse between the alkali metal bicarbonate deodorant ingredient addition step and the cosmetic product container filling and solidifying step. Alkali metal bicarbonate can convert to alkali metal carbonate, carbon dioxide and water at elevated temperatures.

Adding the bicarbonate salt as the last ingredient of the blended formulation, and processing the formulation to the final solid, semi-solid or liquid cosmetic product formation stage within a short time period, are factors which minimize the degradation of the bicarbonate salt ingredient, and the undesirable formation of water and carbon dioxide vapor byproducts. The addition and mixing of the bicarbonate salt ingredient into the formulation, and the dispensing of the formulation into cosmetic containers, can be accomplished as an essentially instantaneous procedure by utilizing an integrated mixing valve nozzle device, such as the type described in U.S. Pat. Nos. 2,816,518; 3,454,198; 3,949,904; 4,318,429; 4,549,813; 5,046,538; 5,094,276; and the like.

The practice of a process for the production of a cosmetic deodorant product can be conducted in conventional equipment, and is readily adaptable to a commercial-scale manufacturing operation.

A present invention cosmetic stick product preferably has a hardness penetration value between about 4–12 millimeters, as determined by American Society For Testing Materials (ASTM) Method D5.

A present invention cosmetic deodorant stick, roll-on or cream product has exceptional properties for treating or preventing perspiration and malodor associated with human underarm perspiration. A present invention cosmetic deodorant formulation can be applied effectively with safety and comfort for reduction of underarm perspiration and offensive odors.

The following Examples are further illustrative of the present invention. The components and specific ingredients are presented as being typical and various modifications can be derived in view of the foregoing disclosure within the scope of the invention.

EXAMPLE I

This Example illustrates a fluidized bed procedure for coating particulate bicarbonate crystallites with a hydrophilic polymer in accordance with the present invention.

A fluidized bed vessel is utilized which is equipped with a Wurster air-suspension coater system (WARF) as described in U.S. Pat. No. 4,568,559 and U.S. Pat. No. 4,877,621.

A coating solution is prepared by dissolving polyethylene glycol (45 g, Poly-G 2000, Olin Corp.), and propylene glycol butyl ether (10 g, PPG 14, Americol) in ethanol (500 g)/water (75 g).

Sodium bicarbonate is utilized as the core matrix type of crystallites. The sodium bicarbonate (Particle Size Technology, Inc.) has an average particle size of about 5 microns, and 90 percent of the particles have a diameter less than 20 microns.

The sodium bicarbonate powder is charged into the coating chamber of the coater system. Compressed air is introduced into the coating chamber, and the polymeric coating solution is sprayed on the air-suspended bicarbonate crystallites, until the coating weight is about 30% of the total dry weight of the coated particles.

The procedure is repeated, except that Hydroxypropylmethylcellulose (Methocel 60 HG, Dow Chemical Co.) is employed as the hydrophilic polymer.

The procedure is repeated, except that maltodextrin (Lodex 10; Durkee Foods) or amylodextrin is employed as the water-soluble polymer, and 0.5 g of a surfactant is included in the solution (polyoxyethylenesorbitan monolaurate; Tween 20; ICI Americas Inc.).

The procedure is repeated except that an 80/20 by weight mixture of polyvinylpyrrolidone/polyvinyl acetate is employed as the crystallite-coating polymer ingredient.

The coated particles consist of a polymer coating on an inner core of a single bicarbonate crystallite or multiple crystallites.

EXAMPLE II

This Example illustrates a procedure for the preparation of an antiperspirant-deodorant cosmetic stick product in accordance with the present invention.

A stainless steel tank is provided which is equipped with turbine agitation.

Silicone oil DC 245 (400 lbs, Dow Corning) and Dow DC 200 (37.50 lbs, Dow Corning) are charged to the mixing tank. Agitation (55–65 RPM) is initiated, and heating the liquid medium to 176° F. is commenced.

During the heating period, the following ingredients are added to the stirred liquid medium:

|  | lbs. |
| --- | --- |
| Lanette 18 DEO[1] | 175.00 |
| Castorwax MP-80[2] | 31.25 |
| ICI G-2162[3] | 6.25 |

[1] Stearyl alcohol; Henkel.
[2] Hydrogenated castor oil; RTD.
[3] PEG 25 PG stearate; ICI.

The mixture is stirred at 176° F. for about 30 minutes until the ingredients are melted and the liquid medium is homogeneous. The stirring speed is reduced to about 35 RPM, then Cyprus Supra A Talc 1625 (18.75 lbs, Cyprus), Reach AZP 908 aluminum-zirconium tetrachlorohydrex glycine (297.50 lbs, Reheis) boron oxide (15 lbs; ultrafine powder) are added. The temperature is maintained at 176° F. for about 40 minutes until the fluid medium is uniform, and then the temperature is lowered to 154° F.

A polymer-coated sodium bicarbonate (148 lbs.) is added with stirring to Silicone oil DC 245 (200 lbs, Dow Corning) in a second mixing tank at a temperature of 154° F. to form a homogeneous suspension medium. The sodium bicarbonate powder is pre-coated with amylodextrin employing a fluidized bed type procedure as described in Example I.

The contents of the two mixing tanks which contain heated fluid medium are transferred to separate fill tanks through a Greer mill, and the fill tanks are connected to a mixing and dispensing nozzle device, of the type described in U.S. Pat. No. 5,094,276. The nozzle device is adapted for homogeneously blending the two separate streams of fluid media, and dispensing a predetermined quantity of the blended fluid.

Plastek 2 oz. bottom-fill stick containers are filled with the blended fluid. The container contents are cooled to a room temperature solid stick over a period of about 45 minutes. The average hardness value of the solid sticks is 7 (ASTM Method D5).

EXAMPLE III

This Example illustrates the preparation of a deodorant roll-on product in accordance with the present invention.

A roll-on formulation is prepared by blending the following proportions of ingredients:

|  | lbs. |
| --- | --- |
| Silicone oil DC 245 | 62.90 |
| Quaternium-18 hectorite clay (Rheox) | 15.00 |
| Potassium bicarbonate[1] | 16.00 |
| Boron oxide[2] | 3.00 |
| Cab-o-Sil fumed silica (Cabot) | 1.60 |
| Propylene carbonate | 1.50 |

[1] Average particle size of 75 microns.
[2] Average particle size of 10 microns.

The roll-on formulation exhibits excellent dimensional stability when packaged and maintained under storage conditions for six months.

EXAMPLE IV

This Example illustrates the preparation of a deodorant cream product in accordance with the present invention.

|  | lbs. |
| --- | --- |
| Cyclomethicone D-5[1] | 36.0 |
| Light mineral oil[2] | 10.0 |
| Permethyl 101A[3] | 10.0 |
| Sodium bicarbonate[4] | 30.0 |
| Boron oxide[5] | 1.5 |
| Boric acid[6] | 0.5 |
| Propylene carbonate | 1.5 |
| Quaternium-18 hectorite | 6.0 |
| Castor wax | 4.5 |

[1] Cyclic polydimethylsiloxane (G. E. Silicones).
[2] Benol white mineral oil (Witco).
[3] Branched chain hydrocarbon fluid (Permethyl Corp.).
[4] Average particle size of 44 microns.
[5] Average particle size of 15 microns.
[6] Average particle size of 80 microns.

All of the ingredients are combined and heated to 45° C. with agitation. The admixture is milled with a Tekmar mill to form a stiff cream.

The cream product is applied to underarm skin surfaces, and it reduces the level of perceived odor, and provides a soothing dry effect.

What is claimed is:

1. A cosmetic deodorant product comprising an organic matrix which contains a homogeneously dispersed particulate phase which comprises (1) between about 0.5–20 weight percent of discrete crystallites of at least one ingredient selected from alkali metal and ammonium bicarbonates, and (2) between about 0.01–5 weight percent of particulate boron oxide desiccant ingredient, based on product weight.

2. A cosmetic deodorant product in accordance with claim 1 which is a cosmetic stick, roll-on or cream formulation.

3. A cosmetic deodorant product in accordance with claim 1 in which the homogeneously dispersed particulate phase contains between about 0.01–3 weight percent of discrete crystallites of boric acid ingredient, based on product weight.

4. A cosmetic deodorant product in accordance with claim 1 in which the homogeneously dispersed particulate phase additionally contains between about 0.1–15 weight percent of discrete crystallites of antiperspirant ingredient, based on product weight.

5. A cosmetic deodorant product in accordance with claim 1 wherein the homogeneously dispersed particulate phase has an average particle size between about 1–200 microns.

6. A cosmetic deodorant product in accordance with claim 1 wherein the crystallites of bicarbonate ingredient are in the form of organic-encapsulated particles.

7. A cosmetic stick product consisting of a solid organic matrix comprising the following parts by weight of ingredients:

| volatile oil | 10–55 |
| liquid emollient | 1–35 |
| low melting point wax | 12–30 | and the solid organic matrix contains a homogeneously dispersed particulate phase which comprises (1) between about 0.5–20 weight percent of discrete crystallites of at least one ingredient selected from alkali metal and ammonium bicarbonates, and (2) between about 0.01–5 weight percent of particulate boron oxide desiccant ingredient, based on product weight.

8. A cosmetic stick product in accordance with claim 7 wherein the volatile oil ingredient comprises a cyclic or linear polydimethylsiloxane containing 3–9 silicon atoms.

9. A cosmetic stick product in accordance with claim 7 wherein the volatile oil ingredient comprises a $C_{12}$–$C_{20}$ branched-chain hydrocarbon.

10. A cosmetic stick product in accordance with claim 7 wherein the liquid emollient ingredient is a water-insoluble organic ester or ether compound.

11. A cosmetic stick product in accordance with claim 7 wherein the wax ingredient is selected from $C_8$–$C_{30}$ alcohol, ester and amide compounds.

12. A cosmetic stick product in accordance with claim 7 wherein the bicarbonate crystallites are sodium, potassium or ammonium bicarbonate or any mixture thereof.

13. A cosmetic stick product in accordance with claim 7 in which the homogeneously dispersed particulate phase containing between about 0.01–3 weight percent of discrete crystallites of boric acid ingredient, based on product weight.

14. A cosmetic stick product in accordance with claim 7 in which the homogeneously dispersed particulate phase additionally contains between about 0.1–20 weight percent of discrete crystallites of antiperspirant ingredient, based on product weight.

15. A cosmetic stick product in accordance with claim 7 wherein the homogeneously dispersed particulate phase has an average particle size between about 1–200 microns.

16. A cosmetic stick product in accordance with claim 7 wherein the crystallites of bicarbonate ingredient are in the form of organic-encapsulated particles, and wherein the encapsulating polymer is a hydrophilic polymer or a water-insoluble polymer or a mixture thereof, and the polymer comprises between about 5–70 weight percent of the dry particle weight.

17. A cosmetic roll-on product consisting of a liquid organic matrix comprising the following parts by weight of ingredients:

| volatile oil | 55–70 |
| liquid emollient | 3–10 | and the liquid organic matrix contains a homogeneously dispersed particulate phase which comprises (1) between about 0.5–20 weight percent of discrete crystallites of at least one ingredient selected from alkali metal and ammonium bicarbonates, and (2) between about 0.01–5 weight percent of particulate boron oxide desiccant ingredient, based on product weight.

18. A cosmetic roll-on product in accordance with claim 17 wherein the volatile oil ingredient comprises a cyclic or linear polydimethylsiloxane containing 3–9 silicon atoms.

19. A cosmetic roll-on product in accordance with claim 17 wherein the volatile oil ingredient comprises a $C_{12}$–$C_{20}$ branched-chain hydrocarbon.

20. A cosmetic roll-on product in accordance with claim 17 wherein the liquid emollient ingredient is a water-insoluble organic ester or ether compound.

21. A cosmetic roll-on product in accordance with claim 17 wherein the wax ingredient is selected from $C_8$–$C_{30}$ alcohol, ester and amide compounds.

22. A cosmetic roll-on product in accordance with claim 17 wherein the bicarbonate crystallites are sodium, potassium or ammonium bicarbonate or any mixture thereof.

23. A cosmetic roll-on product in accordance with claim 17 in which the homogeneously dispersed particulate phase contains between about 0.01–3 weight percent of discrete crystallites of boric acid ingredient, based on product weight.

24. A cosmetic roll-on product in accordance with claim 17 in which the homogeneously dispersed particulate phase additionally contains between about 0.1–20 weight percent of discrete crystallites of antiperspirant ingredient, based on product weight.

25. A cosmetic roll-on product in accordance with claim 17 wherein the homogeneously dispersed particulate phase has an average particle size between about 1–200 microns.

26. A cosmetic roll-on product in accordance with claim 17 wherein the crystallites of bicarbonate ingredient are in the form of organic-encapsulated particles, and wherein the encapsulating polymer is a hydrophilic polymer or a water-insoluble polymer or a mixture thereof, and the polymer comprises between about 5–70 weight percent of the dry particle weight.

27. A method of practicing personal hygiene which comprises applying a claim 1 cosmetic deodorant product to skin surfaces in a deodorant-effective amount.

28. A method in accordance with claim 27 wherein the deodorant product: is a cosmetic stick. roll-on or cream formulation.

* * * * *